(12) United States Patent
Blasi et al.

(10) Patent No.: US 6,462,170 B1
(45) Date of Patent: Oct. 8, 2002

(54) UPAR MIMICKING PEPTIDE

(75) Inventors: Francesco Blasi, Milan (IT); Francesca Fazioli, Ancona (IT); Massimo Resnati, Milan (IT); Nicolai Sidenius, Milan (IT)

(73) Assignees: Fondazione Centro San Raffaele del Monte Tabor, Milan (IT); Universita Degli Studi di Milano, Milan (IT)

(*) Notice: Subject to any disclaimer, the term of this patent is extended or adjusted under 35 U.S.C. 154(b) by 0 days.

(21) Appl. No.: 09/381,244

(22) PCT Filed: Mar. 18, 1998

(86) PCT No.: PCT/EP98/01547

§ 371 (c)(1),
(2), (4) Date: Oct. 20, 1999

(87) PCT Pub. No.: WO98/42733

PCT Pub. Date: Oct. 1, 1998

Related U.S. Application Data

(60) Provisional application No. 60/041,112, filed on Mar. 20, 1997.

(51) Int. Cl.[7] .................. C07K 7/00; A61K 38/00; C12Q 1/00; C12P 21/00
(52) U.S. Cl. .................. 530/300; 435/4; 435/69.7; 435/320.1; 435/325; 435/334; 530/326; 530/327; 530/328; 530/330; 536/23.1; 536/23.4
(58) Field of Search .................. 435/4, 69.7, 320.1, 435/325, 334; 530/300, 326, 327, 328, 330; 536/23.1, 23.4

(56) References Cited

FOREIGN PATENT DOCUMENTS

| WO | WO-86/06100 A1 | * | 10/1986 |
| WO | WO-94/28014 A2 | * | 12/1994 |
| WO | WO-95/07106 A1 | * | 3/1995 |

OTHER PUBLICATIONS

Pyke et al., An alternatively spliced variant of mRNA for the human receptor for urokinase plasminogen activator, FEBS Letters (1994) 326(1–3):69–74.*

Behrendt et al., Domain Interplay in the urokinase receptor, J. Biological Chemistry, (Sep. 12, 1996) 271(37):22885–22894.*

EMBO Journal, vol. 16, No. 24, pp. 7279–7286, XP002072480, Dec. 1997, "A urokinase–sensitive region of the human urokinase receptor is responsible to its chemotactic activity", F. Fazioli et al.

EMBO Journal, vol. 15, No. 7, pp. 1572–1582, XP002072481, Apr. 1996, "Proteolytic cleavage of the urokinase receptor substitutes for the agonist–induced chemotactic effect", M. Resnati et al.

EMBO Journal, vol. 13, No. 17, pp. 3983–3991, XP002072482, 1994, "The effect of antisense inhibition of urokinase receptor in human squamous cell carcinoma on malignancy", Y. Hoh Kook et al.

Trends in Phamacol. Sci., vol. 15, [[/ 25–29, XP002072483, 1994, "uPA and uPAR: new targets for anti–metastatic therapy?", F. Fazioli and F. Blasi.

EMBO Journal, vol. 9, No. 2, pp. 467–474, XP000086848, Feb. 1, 1990, "Cloning and Expression of the Receptor for Human Urokinase Plaminogen Activator, A Central Molecule, etc.", A. Roldan et al.

Biochemistry, vol. 33, No. 30, pp. 8991–8997, XP000574762, Aug. 2, 1994, "Ligand Interaction Between Urokinase–Type Plasminogen Activator and its Receptor etc.", M. Ploug et al.

* cited by examiner

*Primary Examiner*—Karen Cochrane Carlson
*Assistant Examiner*—Holly Schnizer
(74) *Attorney, Agent, or Firm*—Birch, Stewart, Kolasch & Birch, LLP

(57) ABSTRACT

Peptides comprising the SRSRY sequence (SEQ ID NO: 7) derived from the uPAR (urokinase receptor) are endowed with chemotactic activity, making them useful for preventing or activating the migration of cells in a mammal. More particularly, the peptides of the invention are useful for the treatment of cancer, autoimmune diseases, and/or hyperinflammatory diseases and for stimulating wound healing.

6 Claims, 5 Drawing Sheets

A

CHEMOTACTIC and Control uPAR PEPTIDES

Figure 2:
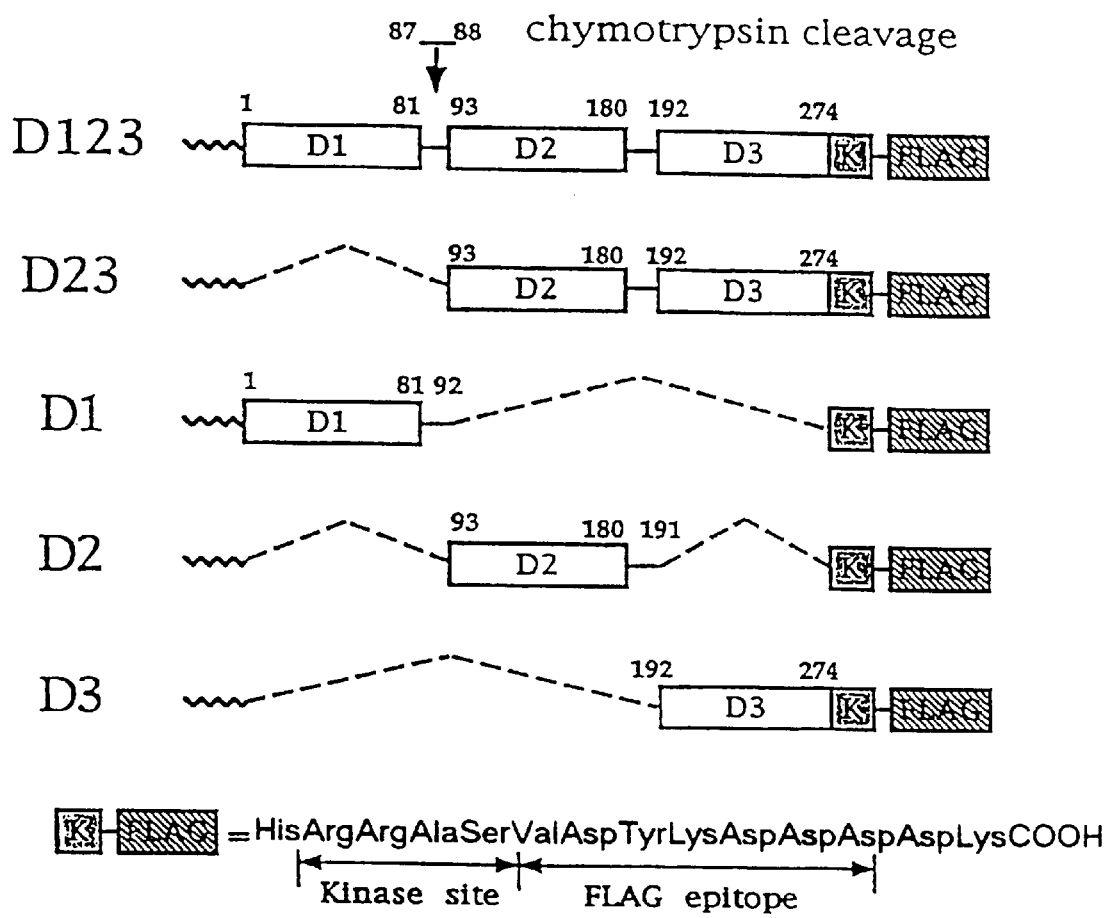

| | |
|---|---|
| peptide 1 (84-95) | AVTYSRSRYLEC |
| peptide 2 (88-95) | SRSRYLEC |
| peptide 3 (301-313) | YTARLWGGTLLT |
| peptide1 scrambled | TLVEYYSRASCR |

B

Conservation of the peptide sequence through species.

SRSRY Human
SRNRY Bovine
PQGRY Mouse
PRGRY Rat

| | 1 | 2 | 3 | 4 | 5 |
|---|---|---|---|---|---|
| Consensus | S/P | R/Q | S/N/G | R | Y |

Fig. 1

UPAR MIMICKING PEPTIDE

This application is the U.S. national phase of PCT EP98/01547 filed Mar. 18, 1998, which claims priority to U.S. Provisional application No. 60/041,112, filed Mar. 20, 1997.

FIELD OF THE INVENTION

The present invention relates to a method for preventing or activating the migration of cells in a mammal, in particular a human. The method comprises the use of synthetic peptides, or of defined recombinant soluble forms of the urokinase receptor to activate the recruitment of inflammatory cells in a mammal, by stimulating a cellular adaptor that mediates the chemotactic activity of uPA. This mechanism does not require the protease activity of urokinase. Actually it by-passes it by acting on a downstream step, namely the interaction of such a peptide or recombinant soluble form of urokinase receptor with a cellular adaptor. Additionally, the reagents produced are also useful to identify and isolate drugs that can inhibit said processes of cell recruitment, and hence may be employed in blocking the malignant phenotype of cancer and of aggressive hyper-or auto-inflammatory diseases.

GENERAL BACKGROUND
Cell Migration and Disease

The response of the human body to noxic stimuli is dependent on the local production of inflammatory molecules as well as on the recruitment of specialized cells that migrate from the blood and the neighbouring tissue into the damaged site. These cells, neutrophils, monocyte-macrophages, lymphocytes and endothelial cells, respond to specific migratory stimuli and build up a defense response that results in the destruction and elimination of the nocive agent or organism. While essential and beneficial for the host defense, this type of response may also prove dangerous for the host or may hamper the success of some therapeutic or preventive approaches like transplantation and vaccination. In fact, a series of severe pathological entities exist which can be ascribed to excess or deficient migratory cell response. For example, immunodeficient patients fail to respond to infective agents and this may be due to inability of the cells to rush to the damaged or infected site. Excess of recruitment, on the other hand, may be responsive of destructive pathologies in which defense cells attack cells and functions of the host, as it happens for example in autoimmune diseases. Failure to properly respond to vaccination, moreover, may also depend on unwanted recruitment of host inflammatory cells that destroy the antigenic cells too quickly to promote an immunological response. The availability of a specific "adjuvant" to natural immunity cells, would be advantageous as it would produce a stronger antibody response.

The malignancy of cancer cells mostly consists in the ability to invade and metastasize at a distance; in this process, however, non-malignant stromal host cells actively participate in establishing the malignant phenotype and hence the destructive and invasive phenotype. While the mechanisms involved are largely unknown, it is clear that stromal cells not only respond to stimuli arriving from the cancer cells but also signal to cancer cells through mechanisms of their own. In order to block the invasive phenotype of cancer, it is thus essential to act both on cancer and on stromal cells.

The Urokinase/urokinase Receptor System

The activity of urokinase (uPA) can be confined to the cell surface by the presence of a specific receptor (uPAR, CD87). uPA is a serine protease important in maintaining the fibrinolytic state of the body as it generates plasmin from plasminogen and hence prevents fibrin deposition. Plasmin is a broad spectrum protease that can destroy many proteins of the extracellular matrix and hence the inter-cellular and cell-to-extracellular matrix connections. UPA and uPAR have long been recognised as regulators of cell migration and hence to be important in inflammation and cancer invasion. In addition to functions connected to its proteolytic activity, uPA has other properties that do not require proteolytic activity, but simply the binding to the receptor. In fact, the proteolytic and the receptor binding activities are separated on the uPA molecule and can be assayed individually (receptor binding in the amino terminal fragment, proteolysis in the carboxy-terminal fragment). Among the functions that do not require the proteolytic moiety of uPA, are the stimulation of mitogenesis, cell migration, adhesion and, in particular, chemotaxis (Gudewicz and Bilboa, 1987; Gyetko et al., 1994; Resnati et al., 1996; Besser et al., 1996).

The specific uPA receptor (uPAR) is a GPI-anchored plasma membrane protein endowed with a very high affinity (Kd of 0.1–1 nM) for uPA, pro-uPA and inhibited forms of uPA, like the uPA-PAI-1 complex (Fazioli and Blasi, 1994). In addition to uPA, uPAR also binds vitronectin with an about 10–20 nM affinity as well as integrins. Structurally, uPAR is formed by three repeats of about 90 amino acid residues connected by two linker regions (Danø, Blasi et al., 1990; Behrendt et al., 1991) which define functionally and structurally different domains: the amino terminal domain (D1) contains the uPA binding site, while the carboxyterminal region containing domains D2 and D3 binds vitronectin. However, the integrity of the three-domains structure is necessary for high affinity binding to uPA at least with the purified, soluble protein (Danø et al., 1994). To date, no information has been provided as to the function of the linker regions.

uPAR is expressed in circulating blood cells, in particular monocytes, neutrophils and T-lymphocytes but not in erythrocytes or B-lymphocytes., In addition, uPAR is a target gene in lymphocytes and macrophage activation (CD87). Indeed, monocytes and monocyte-like cells (like HL60, U937) express uPAR, or are induced to overexpress uPAR by a variety of cytokines and other agents, like phorbol ester PMA, phytohemagglutinin, bacterial liposaccharide, TGFb1/vitamin D3, GM-CSF, IFNg, TNFa and others. In human T-lymphocytes, stimulation of the TCR/CD3 complex, lymphokines IL2, IL4, IL7 or the concomitant activation of the T cell receptor and integrins engagement, all induce uPAR expression (Nykjmr et al., 1994; Bianchi et al., 1996). It is also noteworthy, that tumor infiltrating T-lymphocytes heavily express UPA-R and some of the properties of the activated T-lymphocytes, in particular their migration through reconstituted basement membranes, appear to be at least in part uPA- and uPAR-dependent (Bianchi et al., 1996). In view of the important contribution of stromal cells to the invasiveness of cancer, it is also important to stress that macrophages present in human breast cancer and other cancers, where the level of uPAR production by the overall tumor importantly contributes to its malignancy, express high levels of uPAR (Brunner et al., 1996). The cooperation between stromal and cancer cells in cancer invasiveness, implies that high expression of uPAR by cancer or stromal cells, can affect cell prognosis possibly through different mechanisms depending on the overexpressing cell-type.

uPA/uPAR and Chemotaxis

Cooperation between cancer and stromal cells poses the problem of how uPAR expression on stromal cells influences the malignancy of cancer cells. Since the uPA/uPAR system has chemotactic activity, the production of uPAR by stromal cells can attract cancer cells through a chemokine like action. Indeed, chemokines produced by certain cells are anchored to a presentation molecule in the extracellular matrix and attract other cells having specific receptors (Schall and Bacon, 1996). The information available on the uPA/uPAR system supports this possibility.

DISCLOSURE OF THE INVENTION
uPA/uPAR and Chemotaxis

Stimulation of chemotaxis in monocyte-like cells, fibroblasts and some cancer cells requires the specific cell surface uPAR (CD87) which mediates the chemoattractant activity of uPA (Resnati et al., 199.6). Chemotaxis by uPA does not require its protease activity, but only the occupancy of its receptor, and can be reproduced with the enzymatically inactive receptor binding moiety ATF (amino terminal fragment), pro-uPA and by chymotrypsin-cleaved soluble uPAR (Resnati et al., 1996). In mouse, the importance of this system in cell recruitment in vivo is shown by the fact that uPA is essential for the inflammatory response; indeed, mice lacking the uPA gene are highly defective in the response to bacterial and possibly other infections, and are incapable of recruiting T-lymphocytes and macrophages to the site of infection (Gyetko et al., 1996). In man, uPA and uPAR are induced during T cells activation and directly contribute to the in vitro migration of human T cells (Nykjær et al., 15 1994; Bianchi et al.,1996). Moreover, tumor infiltrating T-lymphocytes heavily express uPAR (Bianchi et al., 1996).

uPA-dependent chemotaxis is mediated by the activation of src-family tyrosine kinases (i.e. Hck in monocytes and Src in fibroblasts). The mechanism involved requires that uPA modifies uPAR conformation such that it can bind to a still unidentified adaptor. Indeed, in cells lacking uPAR, a mixture of fragments generated by cleaving a soluble, recombinant uPAR with chymotrypsin, has a very potent chemoattractant activity (IC50 of 10–20 pM) (Resnati et al., 1996).

In Boyden chamber-based assays, uPA or its derivatives induce migration through a chemotactic gradient in bovine adrenal capillary endothelial cells, keratinocytic cell lines, monocytes, monocyte-like cells, fibroblasts cell lines, and in neutrophils both in vitro and in vivo (Besser et al., 1996; Resnati et al., 1996). The involvement of uPAR in chemotaxis is not only a direct one, but may also be indirect by interfering with the chemotaxis induced by other chemokines. Exposure of human neutrophils to a chemotactic gradient of FMLP or MCP-1 chemokine localizes uPAR to the leading edge of the migrating cell; anti-uPAR antibodies ablate the chemotactic activity. The chemotactic effect of FMLP or MCP-1 does not require the proteolytic activity of uPA, but uPAR occupancy is absolutely required for chemotaxis as uPAR antibodies or antisense RNA expression totally abolishes FMLP or MCP-1 activity.

The steps between the binding of chemokines to chemokine receptors and cell movements, are many and complex: signal transduction, reorganization of cytoskeleton, formation of focal adhesions, attachment and detachment from the substrate with pseudopodal extension and retraction to effect directional migration (Premack and Schall, 1996). The chemotactic activity of uPAR has many of the properties of chemokines. Interaction between uPAR and integrins has been observed in neutrophils: the leucocyte integrin CD11b/CD18, aMb2, also known as the complement receptor type-3 (CR3) has been shown to physically associate with uPAR. This interaction is reversible and correlates with cell shape. In resting cells, uPAR and CR3 are co-localized, but following spontaneous cell polarization and migration, the two receptors dissociate, CR3 concentrates in the uropods and uPAR in the lamellipodia of polarized cells. Since CR3 regulates cell adhesion, chemotaxis and cell migration into inflammatory sites, the interaction with uPAR may be central to all these functions and hence to the cell-recruitment action of uPA/uPAR. No information however is available as to whether this integrin (or others) is directly involved in mediating the uPAR chemotactic signal, i.e. whether this integrin is the so far unidentified adaptor.

Activation of migration by uPAR occupancy is observed also in epithelial cell lines where uPAR associates with a protein kinase that can serine-phosphorylate two cytokeratins, CK18 and CK8. The enzyme responsible is possibly the protein kinase Cz, since the process is independent from Ca2+, resistant to PMA down modulation and since the kinase can be specifically immuno-recognized. In vivo, CK18 and CK8 are phosphorylated on serine and uPAR occupancy elicits a time-dependent increase in phosphorylation of CK8, cell shape changes and redistribution of cytokeratin filaments. Pro-uPA treatment caused rounding up of the cells and reduction of their diameter. In control cells, cytokeratins were distributed in a lattice array parallel to the surface of the coverslips; upon treatment with pro-uPA, little or no cytokeratins were observed in filament form. These data tie together the migratory effect of pro-uPA, the activation of protein kinase C and the cell shape changes. Tyrosine-phosphorylation of a non-characterized 35 kDa protein occurs upon binding of pro-uPA to U937 myeloid cells. In these cells, occupancy of uPAR promotes cell adhesion during PMA-induced differentiation. It has been shown that uPAR directly binds vitronectin and promotes cell adhesion. Moreover, uPAR directly interferes with the substrate recognition of adhesion receptors by forming complexes directly with the beta integrins, and hence promoting adhesion on vitronectin and inhibiting adhesion on fibronectin (Wei et al., 1996). Indeed, uPAR can be co-immunoprecipitated with anti-integrins IgG. The effect of uPAR on cell adhesion is also in line with its chemokine-like activity. A direct interaction of uPAR with integrins is suggested by their co-immunoprecipitation and by the finding of peptides that specifically inhibit the co-immunoprecipitation without interfering with the binding of uPA or vitronectin to uPAR (Wei et al., 1996). Therefore, integrins might represent the described adaptor suggested by Resnati et al. (1996). In this respect, the uPAR-like small molecules to be described in this application, have whatsoever no connection, either structural or conceptual, with the peptide identified by Wei et al. (1996).

In monocytes and fibroblasts, occupancy of uPAR induces chemotaxis and the effect does not require extracellular proteolysis (Resnati et al., 1996). In this system, ATF binding causes a time-dependent and transient activation of a tyrosine kinase of the Src family, the p56/p58 Hck. In addition, uPAR itself associates with tyrosine kinases, through what appears to be a transmembrane-adaptor-mediated mechanism. Indeed, cells lacking uPAR, and therefore not responsive to ATF, are capable of chemotaxis when challenged with a mixture of chymotryptic fragments of soluble uPAR (chymotrypsin cleaves uPAR in two fragments between domain D1 and D2) (Resnati et al., 1996). This effect also occurs in fibroblasts derived from uPAR–/– mice. Therefore, uPAR can recognize a cell surface molecule which in turn is capable of mediating signal transduction. The occupancy of surface uPAR must in fact expose binding sites for the unidentified adaptor and hence transform uPAR from a receptor into a ligand. The role of tyrosine kinases in uPAR-dependent chemotaxis is also shown by the effect of tyrosine kinase inhibitors that prevent the chemotactic response to ATF, and by the failure of primary src-/-fibroblasts to respond to the soluble, cleaved uPAR (Resnati, Blasi and Fazioli, unpublished). Interestingly, while uPA binding to uPAR is strictly species-specific, human uPAR acts as a chemoattractant as efficiently on human as on murine cells. In particular, chymotrypsin-cleaved soluble uPAR has an IC50 of about 20 pM (Resnati et al., 1996).

The Chemoattractant Property of uPAR as a Target for Novel Drugs Acting Downstream of the uPA/uPAR Interaction The uPA/uPAR system is involved in cancer cell invasiveness, and also in inflammation and other diseases (Danø et al., 1990). And in fact, the block of uPA/uPAR interaction by specific antagonists, or the reduction of uPAR synthesis by antisense gene expression leads to a drastic reduction of the migratory properties of cancer cells (Fazioli and Blasi, 1994). In human cancer, the expression level of the components of the system, uPA, PAI-1 and uPAR, directly relates to the malignancy of the disease and its prognosis (Brünner et al., 1996). In fact, many if not all solid cancers have already released metastatic cells which are found in the bone marrow. The presence of uPAR-positive metastatic cells at the time of diagnosis represents a sign of extreme likelihood of poor prognosis, while the presence of metastatic cells per se does not.

On the basis of the above, uPAR appears to be a specific target for novel types of drugs that might interfere with the process of inflammation or of cancer invasiveness. Two different possibilities are open: to block uPAR by interfering with uPA binding (uPAR antagonists), or to prevent the direct transduction of a migratory signal, via interaction with other molecules, bypassing the step of the interaction between uPA and uPAR. Drugs preventing the binding of uPAR to the before mentioned adaptor should also prevent chemotaxis via uPAR. Therefore, antagonists of the uPAR/adaptor interaction should block or decrease the migration of cells and hence might be useful in diseases where this decrease or block is advantageous, like cancer, autoimmune and excess-inflammatory reactions.

uPAR as Target for Drugs Enhancing the Recruitment of Inflammatory Cells

The recruitment of cells via the uPA-uPAR interaction suggests that drugs should be found which promote cell recruitment by binding to uPAR. And indeed, uPA derivatives like the amino terminal fragment ATF, pro-uPA or possibly also synthetic peptides that cover the uPAR-binding region of uPA are in fact capable of substituting for uPA in various functions not requiring uPA proteolytic activity (see for example, Fazioli and Blasi, 1994; Besser et al., 1996, Resnati et al., 1996). On the other hand, since uPA binding to uPAR causes a conformational change that transforms uPAR from a receptor for uPA into a ligand for a still unidentified membrane adaptor (Resnati, et al. 1996), an alternative possibility of enhancing cell recruitment would be to bypass the first step, i.e. the uPA-uPAR binding step, and stimulate cell migration by acting at the level of the unidentified adaptor with uPAR itself or specific uPAR-like agonists. These agonists might therefore be useful in diseases in which the recruitment of cells is blocked by genetic or acquired malfunctions upstream of the uPAR/adaptor interaction. Also, the availability of such drugs might be advantageous in connection with increasing the immunogenicity of various antigens, for example in vaccination, as it might act like an adjuvant by recruiting cells responsible of natural immunity.

uPAR as Target for Controlling HIV Infection uPAR is an activation antigen in both T-lymphocytes and in monocytes (Nykjar et al., 1994; Bianchi et al., 1996), i.e. in cells capable of active migration and in which HIV can replicate. While CD3-positive circulating lymphocytes do not or only weakly express uPAR, CD8+ T lymphocytes of patients of AIDS and other viral diseases display a high expression of uPAR, and in several of these patients as many as 80% of their T-lymphocytes are high expressers (Nykjar et al., 1994). A fraction of persons remain uninfected by HIV despite multiple high-risk sexual exposure, and this is connected with the presence of HIV suppressive facfors in their blood (Paxton et al., 1996). Several chemokines have been identified as HIV-suppressive facfors produced by CD8+ T cells (Cocchi et al., 1996) and these chemokines represent novel targets for AIDS therapy. Soluble forms of uPAR exist in the blood and uPAR is in fact cleaved in cell lines and in cancer tissues. Since cleavage activates the chemotactic activity of soluble uPAR (Resnati et al., 1996), these soluble, cleaved forms might, like actual chemokines, also interfere with the infectivity or survival of HIV. If a cleaved form of soluble uPAR is also involved in HIV infectivity or resistance, it might represent a target for a novel type of therapy in cases of AIDS.

uPAR as Target for Drugs Enhancing Wound Healing

Excessive fibrin deposits are observed in plasminogen-deficient, uPA-deficient and in the double uPAR/tPA-deficient mice and these mice are also deficient in skin wound healing (Carmeliet and Collen, 1996). Several mechanisms may be active in this phenomenon, including chemotaxis, since uPAR is localized at the leading edge of migrating keratinocytes during re-epithelization of mouse skin wounds. The importance of monocytes and macrophages in the process of wound healing makes it even more likely that this process might be augmented by a uPAR agonist capable of reproducing its chemoattractant property.

Novel Approach to Blocking uPAR

So far, approaches directed to block the effect of uPAR in cell migration have been limited to the search of uPAR antagonists, i.e. drugs that prevent the binding of uPA to uPAR. In general, such drugs are also expected to inhibit cell surface proteolytic activity. However, binding of uPA to uPAR stimulates chemotaxis by transforming this molecule from a receptor into a ligand for an adaptor (Resnati et al., 1996). Therefore, the identification of a small molecule that can mimic the chemotactic activity of uPAR gives a new handle to control the uPAR-dependent reactions, independent of its occupancy by uPA. In relation to the present invention, such small molecules have been discovered and characterized. They act downstream of the uPA/uPAR interaction and therefore have no effect on cell surface proteolytic activity. These small molecules can be applied both in cases of deficient cell recruitment and migration (as stimulators of the process), and in cases of excess cell recruitment and migration. In the latter case, the uPAR-like small molecules can be employed to identify suitable inhibitors of the uPAR-adaptor interaction.

uPA is essential for inflammatory cell recruitment, binds uPAR and induces chemotaxis by direct signalling in a uPAR-dependent way. In this function uPAR interacts with an unidentified adaptor molecule, and in fact a mixture of chymotryptic fragments of soluble uPAR has chemoattracting activity. The present invention is based upon the discovery of the mechanism through which uPAR activates chemotaxis. First the region of uPAR inducing chemotaxis was identified. As shown in example 1, soluble fragments of uPAR were produced either by separation of chymotrypsin-cleaved uPAR, or by recombinant DNA technology, and were used in a chemotaxis assay to locate the region of uPAR responsible for the chemoattracting activity on THP-1 cells. Such a region (residues 88–92 of uPAR) was localized in the linker region between domain D1 and D2. In fact, the chemotactic activity was found either in domain D1 or D2, whenever they included this linker region: carboxyterminally of domain D1, or aminoterminally of domain D2. In example 2, the chemotactic activity of uPAR was reproduced using synthetic peptides including the 88–92 uPAR sequence of uPAR, on human THP-1 monocytoid cells (and murine LB6 fibroblastic cells). Synthetic molecules (peptides 1 and 2) including the sequence SRSRY (ser-arg-ser-arg-tyr) (SEQ ID NO:7) had a very potent chemotactic activity at concentrations as low as 0.1 pM. Control peptides had no activity, in particular a peptide covering the carboxy-terminal sequence deduced from uPAR cDNA, and a peptide having the same amino acid composition as peptide 1 but a scrambled sequence. In example 3, we show that peptide 1 stimulates chemotaxis through the same mechanism employed by the ligand uPA, or by the mixture of chymotrypsin fragments of the soluble uPAR. Peptide 1, in fact, activates Hck tyrosine kinase of THP-1 cells with the same time-course and concentration dependence observed with the mixture of chymotrypsin fragments of soluble uPAR. Example 4 shows how to practically identify inhibitors of uPAR by employing a simple panning assay using uPAR mimicking peptides, i.e. peptide 1 and 2 of the invention.

One aspect of the present invention relates to a method of stimulating or increasing the chemotactic activity of a cell, comprising adding a chymotrypsin-cleaved suPAR peptide or a functional analogue of said peptide.

Within the scope of the uPAR peptides according to the present invention are uPAR peptides derived from uPAR found in mammalian species, such as human, bovine, murine and rat.

In the present context, the term "functional analogue" means a peptide with an amino acid sequence which is not identical to a chymotrypsin-cleaved suPAR peptide, but which has a substantially identical effect with respect to stimulating or increasing the chemotactic activity of a cell. This effect will typically be tested in an assay such as the one described in example 1. The increase in chemotactic activity in such an assay is preferably at least 100% of control, more preferably at least 200% of control, even more preferably at least 400% of control.

Non-limiting examples of functional analogues of the human uPAR chemotatactic activity are:

ser-arg-ser-arg-tyr (SEQ ID NO:7)
ser-arg-asn-arg-tyr (SEQ ID NO:8)
ser-arg-gly-arg-tyr (SEQ ID NO:9)
ser-gln-ser-arg-tyr (SEQ ID NO:10)
ser-gln-asn-arg-tyr (SEQ ID NO:11)
ser-gln-gly-arg-tyr (SEQ ID NO:12)
pro-arg-ser-arg-tyr (SEQ ID NO:13)
pro-arg-asn-arg-tyr (SEQ ID NO:14)
pro-arg-gly-arg-tyr (SEQ ID NO:15)
pro-gln-ser-arg-tyr (SEQ ID NO:16)
pro-gln-asn-arg-tyr (SEQ ID NO:17)
pro-gln-gly-arg-tyr (SEQ ID NO:18)

Other molecules which contain the above listed functional analogues and have an effect in a chemotactic assay will also be functional analogues within the scope of the present invention, as well as peptides or peptoids having a similar sequence (e.g. 400%–80% sequence identity, such as 60%, 66%, 75% or 80% sequence similarity with any of the listed peptides) as any of the listed peptides and which exhibit an effect in the assay.

Another aspect of the present invention thus relates to a peptoid analogue of the peptide with the sequence SRSRY (SEQ ID NO:7) comprising one or more non-naturally occurring amino acids. The peptoid analogues according to the invention can for example be prepared by using peptide synthesis methods, such as the method described by Merrifield. 1963. The synthesis may include any number of non-naturally occurring amino acids and optionally also including one or more naturally occurring amino acids in the preparation. The peptides and functional analogues of the invention can be added, in an effective amount, directly to cells for to an individual, such as a human patient, who harbours the cells in which chemotactic activity can be stimulated or increased.

A very important aspect of the present invention relates to peptides of the invention. Such peptides are a peptide with the sequence SRSRY (SEQ ID NO:7) or a functional analogue thereof and a peptide with the sequence AVTYSRSRYLEC (SEQ ID NO:1) and a peptide with the sequence SRSRYLEC (SEQ ID NO:3).

A particularly preferred embodiment of the present invention relates to a recombinant fusion protein, comprising one or more of the peptide species according to the invention and optionally additionally comprising one or more of the peptide species according to the invention.

Functional analogues, according to the invention, which are prepared using peptide synthesis are within the scope of the present invention. Functional analogues, according to the invention, which are prepared by using other methods than peptide synthesis, such as recombinant expression, are also within the scope of the present invention.

A further aspect of the present invention is a method of stimulating or increasing a local inflammatory response, comprising adding a chymotrypsin-cleaved fragment, or mixture of fragments, of uPAR, said fragment or mixture of fragments comprising an SRSRY (SEQ ID NO:7) peptide, or a functional analogue of said peptide.

In the present context, the term "stimulating or increasing local inflammatory response" means that one or more characteristics of an inflammatory response can be measured to be stimulated or increased. Such characteristics will typically be release of cytokines by T-lymphocytes or monocyte-macrophages, increase of chemotactic activity, ability to cause a local recruitment of lymphocytes/monocytes upon subcutaneous administration in a suitable laboratory animal, etc. In this particular case, the use of uPA-deficient mice is particularly favourable as these mice have a very low anti-inflammatory response. Methods to measure these activities are available routinely, and increases of such activities as mentioned of at least 50% are considered significant, preferably at least 80% even more preferably at least 100%.

Another important aspect of the present invention is a method of stimulating or increasing the chemotactic activity of a cell, comprising adding a peptide comprising the sequence SRSRY (SEQ ID NO:7)or a functional analogue of said peptide.

A further aspect of the present invention is a method of stimulating or increasing wound healing, comprising adding a chymotrypsin-cleaved suPAR peptide or a functional analogue of said peptide. A peptide comprising the sequence SRSRY (SEQ ID NO:7) or a functional analogue of said peptide can be added according to the invention.

In the present context, the term "stimulating or increasing wound healing" means that at least one of the physiological characteristics or processes involved in healing of various types of wounds in an individual, such as a human, is substantially stimulated or increased. One way of quantifying such stimulation or increase in wound healing comprises measuring wound healing in a plasminogen-deficient or even a normal mouse, and identifying the time required for 50% healing. A reduction of the time of healing, upon addition of an effective amount of a composition comprising suPAR peptide, of at least 20%, preferably at least 50%, would represent a substantial wound healing stimulation.

An important aspect of the present invention relates to a method of stimulating the kinase activity of $p56/p59^{hck}$ comprising adding a chymotrypsin-cleaved suPAR peptide or a functional analogue of said peptide or comprising adding a peptide comprising the sequence SRSRY (SEQ ID NO:7) or a functional analogue of said peptide.

In the present context, the term "stimulating the kinase activity" means substantially increasing the ability of $p56/p59^{hck}$ to phosphorylate a protein substrate. This will typically be measured using in vitro assays as the ones described in example 3. Quantification of such an effect might be obtained by cutting the bands from a gel such as the one showed in FIG. 5, and subsequently measuring the 32P-radioactivity, after normalization.

A very important aspect of the present invention relates to a method of testing whether a compound is capable of stimulating the binding between a chymotrypsin-cleaved soluble form of u-PAR and a cellular adaptor, said method comprising adding an effective amount of the compound to a test system comprising cells lacking endogenous u-PAR and measuring chemotactic activity; if chemotactic activity is present, then the compound is capable of stimulating said binding.

In the present context the term "stimulating the binding" should be taken to mean increasing the binding in an assay, substantially resembling the above described, by at least 20%, preferably at least 30%, more preferably by at least 40%, even more preferably by at least 60%.

In another aspect, the present invention relates to a compound which is capable of stimulating the binding between a chymotrypsin-cleaved soluble form of uPAR and a cellular adaptor which has been selected by the method of the invention as described above.

A particularly important aspect of the present invention relates to a method of testing whether a compound is capable of blocking or inhibiting the binding between a chymotrypsin-cleaved soluble form of uPAR and a cellular adaptor, said method comprising adding chymotrypsin-cleaved soluble form of uPAR and an effective amount of the compound to a test system comprising cells lacking endogenous uPAR and measuring chemotactic activity. If chemotactic activity is inhibited or prevented, then the compound is capable of blocking said binding.

In the present context the term "blocking or inhibiting the binding" should be taken to mean decreasing the binding in an assay, substantially resembling the above described, by at least 20%, preferably at least 30%, more preferably by at least 40%, even more preferably by at least 60%.

In a further aspect, the present invention relates to a compound which is capable of blocking or inhibiting the binding between a chymotrypsin-cleaved soluble form of uPAR and a cellular adaptor which has been selected by the method of the invention as described above.

An important embodiment of the present invention is a compound according to the invention for the treatment of cancer, autoimmune disease and/or hyper-inflammatory diseases. A compound which is capable of blocking or inhibiting the binding between a chymotrypsin-cleaved soluble form of uPAR and a cellular adaptor would according to the invention be administered to an individual, such as a human patient, in need thereof in a pharmaceutically acceptable form and in a pharmaceutically effective amount.

A very important aspect of the present invention relates to a method of screening compounds for potential anti-inflammatory or anti-migratory properties. The method according to the invention comprises (a) coating a plastic surface which does not normally bind mammalian cells with an effective amount of a peptide according to the invention, (b) exposing selected mammalian cells to the coated surface for 30–300 minutes at 37 C., in the presence or absence of a potentially inhibitory compound, and (c) testing the ability of the cells to bind to the peptide coated surface by microscopic inspection or Coomassie Blue staining of the plates; if cellular binding is inhibited or prevented, then the compound is capable of blocking said binding and is a potential anti-inflammatory or anti-migratory agent.

In a further aspect, the present invention relates to oligo nucleotides, in particular oligonucleotides encoding the peptides given by SEQ ID NO: 1 and SEQ ID NO: 3.

Another aspect of the present invention relates to the use of an oligonucleotide according to the invention, for the recombinant expression of peptides for use in the screening of compounds according to the invention.

Preferred embodiments of the present invention relate to use of oligonucleotides according to the invention, wherein the recombinant expression is performed in an expression system chosen from the group consisting of an E. coli expression system, a yeast expression system, a mammalian expression system or an insect cell expression system.

When using the oligonucleotides according to the invention as the basis for preparing peptides according to the invention by performing recombinant expression, it is preferred to combine said oligo nucleotides with nucleic acid sequences, such as regulatory sequences, which enable. the expression system of choice to express large amounts of peptide.

A particularly important aspect of the present invention relates to a method of stimulating or increasing anti-tumour immunity in autologous bone marrow transplantation treatment of an individual, such as a human patient, bearing tumours, comprising modifying tumour cells by transfecting them with a eukaryotic vector expressing a nucleic acid sequence encoding the peptide SRSRY (SEQ ID NO:7), or a functional analogue thereof.

In the present context, the term "anti-tumor immunity" means the set of cellular and chemical reactions which an organism can organize with the aim of rejecting a tumor. In this respect, the production of cytokines and chemokines is of major importance as it will drive the recruitment and the functional activation of cells that can specifically attack the tumor cells and hence destroy it.

Another important aspect of the present invention relates to a method of stimulating or increasing cellular immunity in an individual, such as a human patient, who is immunodeficient, said method comprising adding a chymotrypsin-cleaved suPAR, said suPAR comprising the peptide SRSRY (SEQ ID NO:7), or a functional analogue thereof.

In the present context, the term "cellular immunity" means the recruitment and the functional activation of immune cells, such as T-lymphocytes, NK-cells, B-lymphocytes, macrophages etc.

In the present context, the term "immunodeficient" means that the immune system of an individual is compromised and thus can be said to function at a sub-normal level with respect to at least some of the systems reactions.

Yet another aspect of the present invention relates to a method of vaccinating a subject, such as a human patient, suffering from tumours, with the aim of stimulating an anti-tumour T cell response, said method comprising vaccination of said subject with a human tumour cell line compatible on both the histotype and the HLA-A2 basis and modified so as to release the chemotactic region of the human or murine or bovine or rat uPAR, said chemotactic region being a fusion peptide or a domain of uPAR containing the SRSRY (SEQ ID NO:7) peptide or a functional analogue thereof.

A preferred embodiment of the present invention relates to a method according to invention, wherein vaccination is carried out by using autologous tumor cells.

A very important aspect of the present invention relates to a method of exploiting the cellular immunity of uPAR derivatives or peptides of the present invention to kill tumour cells, said method comprising injecting a tumour-bearing subject, such as a human patient, with tumour-targeted cells modified to express the chemotactic region of uPAR from human, bovine, murine or rat, or any other uPAR having substantially the same properties, said method further comprising fusing the target vector to said region, being a peptide or a domain of uPAR containing the SRSRY (SEQ ID NO:7) peptide, or a functional analogue thereof.

In the present context the term "uPAR derivatives" is used as defined in WO 90/12091, whereas the term "tumour-targeted cells" means cells that, naturally or because they are specially engineered, can be injected into an individual and will specifically interact with tumour cells of said individual.

LEGENDS TO FIGURES

FIG. 1 Part A of this figure shows the sequence of active peptides 1 (SEQ ID NO:1) and 2 (SEQ ID NO:2) reproducing sequences of human uPAR, and the scrambled version of peptide 1 (SEQ ID NO:4) that was employed as a negative control employed in Example 2. Obviously the sequence SRSRYLEC (SEQ ID NO:3) is in common between the peptides 1 and 2. However, the active region can be further delimited since experiments from Example 1 show that the presence of the sequence SRSRY (SEQ ID NO:7) either carboxyterminal to domain D1, or aminoterminal to domain D2,3 confers to these peptides an otherwise absent chemotactic activity. The sequence SRSRY (SEQ ID NO:7) is present in human uPAR between positions 88 and 92. Part B of this figure shows the sequence of the active peptide region in rat (SEQ ID NO:15), mouse (SEQ ID NO:7) and bovine (SEQ ID NO:8) uPAR and its comparison with that of human uPAR. It also shows a preliminary consensus sequence that indicates that the fourth and fifth residues are always conserved, the first and second residues show a conservative change while the third residue appears to be more freely substituted.

FIG. 2. This figure shows a scheme depicting the structure of various soluble forms of uPAR to be employed in Example 1. Schematic representation of the soluble three-domain uPAR (D123) and the four deletion mutants. The number indicate amino acids residues according to the human uPAR sequence deduced from cDNA (Roldan et al., 1990) using as number one the first residue after the signal sequence. Each construct was named on the basis of which of the three domains was still retained: D123 is the symbol for suPAR containing residues 1–274 and being secreted in a soluble form. Each construct contains at the 3' end a FLAGTM (SEQ ID NO:6) epitope which is employed for purification of the proteins onto a commercial antibody-affinity column.

Figure 3:
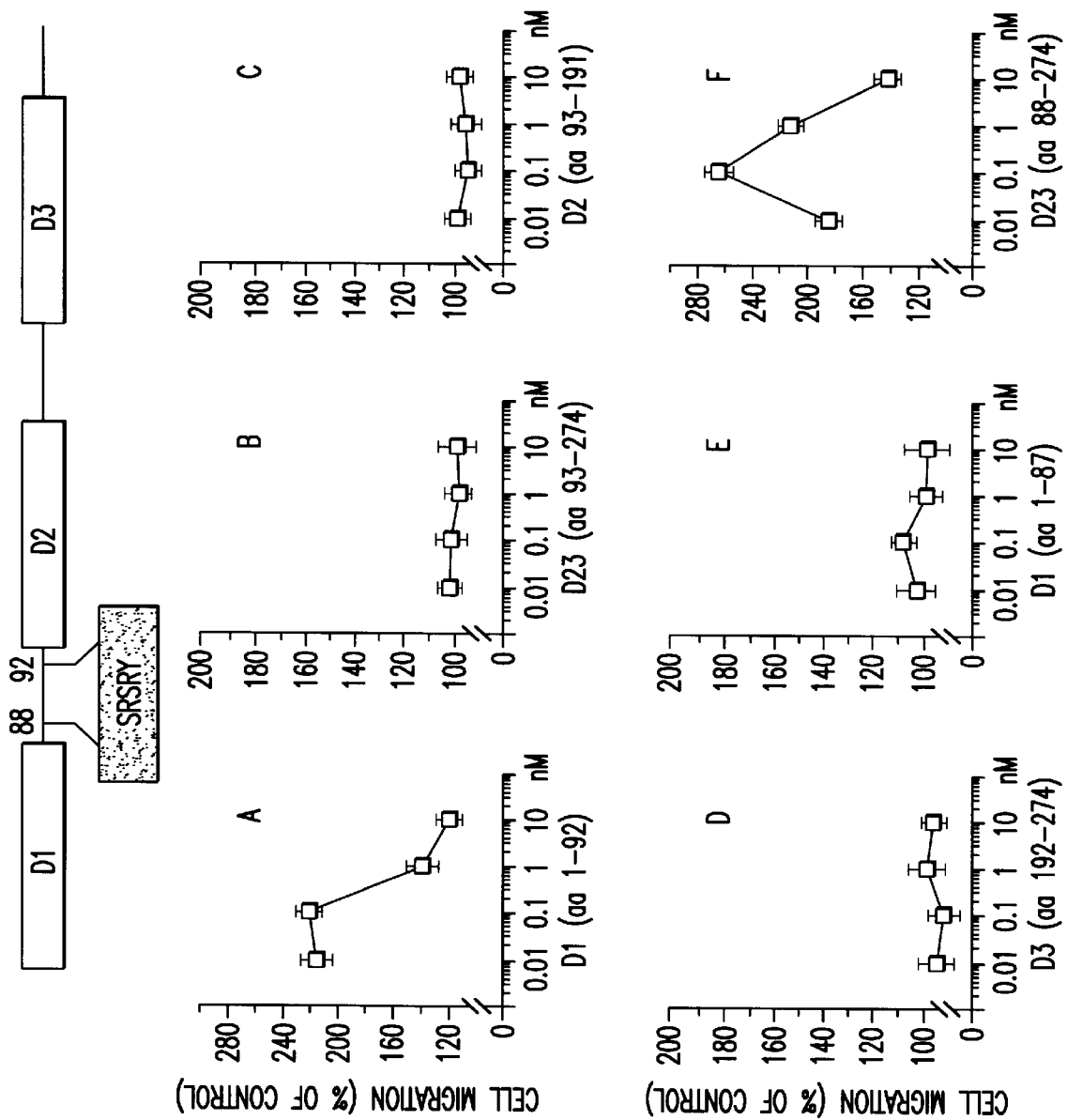

FIG. 3. This figure shows the chemotactic response of THP-1 cells to fragments or mutants of soluble uPAR. For each set of experiments, migration toward the assay medium served as control (random cell migration) and is referred to as 100% migration. All experiments were performed in triplicate; the number of cells counted per high power field (ten fields for each condition) is expressed as percent of the control values. The proteins were purified as described in the Methods section. Data points represent the mean of three independent experiments (+SEM). The constructs used are depicted in FIG. 2.

Figure 4:
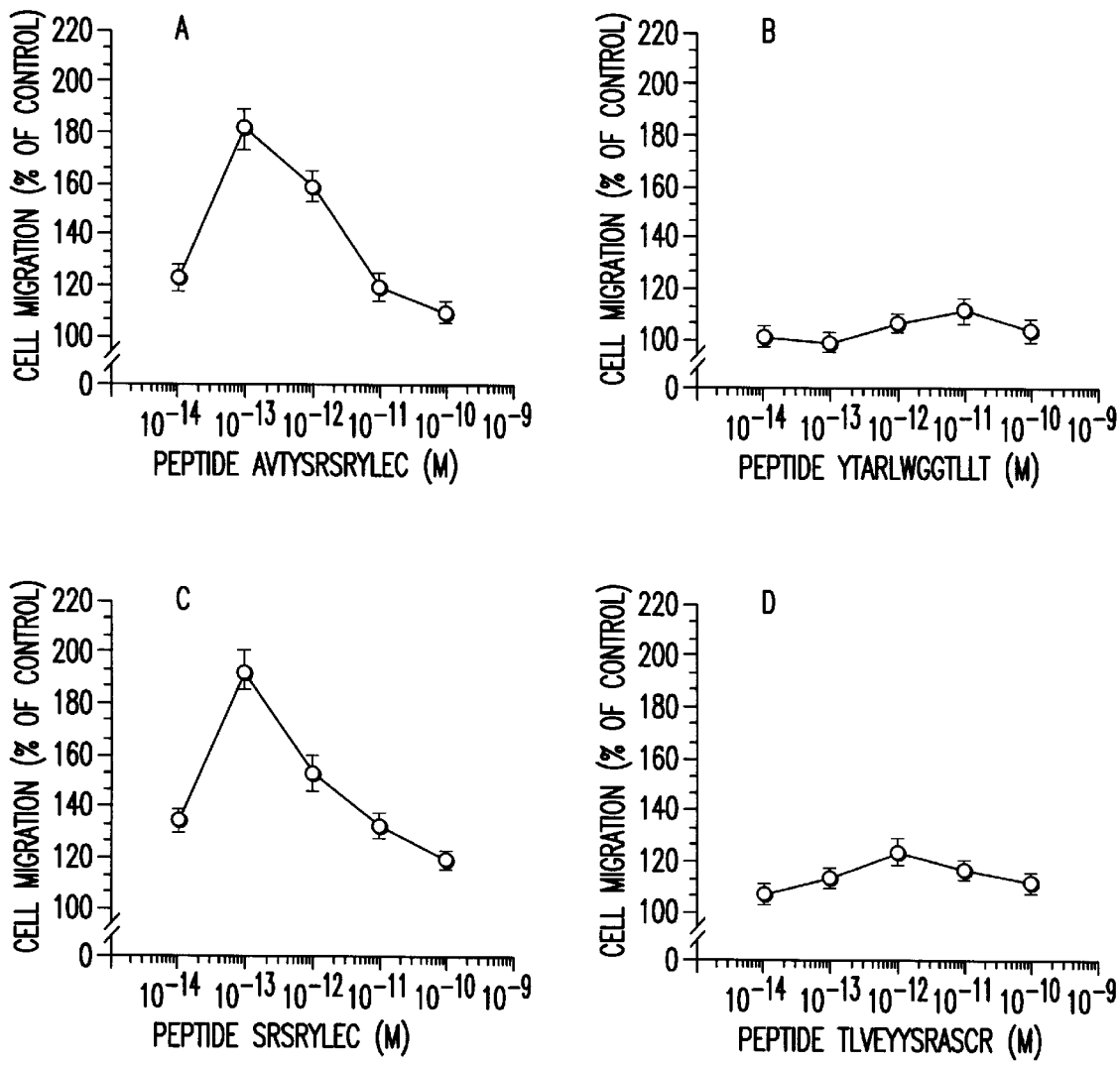

FIG. 4. In this figure, the chemotactic effect of synthetic peptides on THP-1 cells is shown. Peptides 1 and 2 show very potent activity, while peptide 3 or peptide-1 scrambled do not. Dose-dependent chemotactic response of THP-1 cells to peptide 1 (AVTYSRSRYLEC (SEQ ID NO:1), (aa 84–95) (panel A), peptide YTARLWGGTLLT (SEQ ID NO:2) (aa 302–313 of uPAR) (panel B), peptide (SRSRYLEC (SEQ ID NO:3), aa 88–95 of uPAR) (panel C) corresponding to the uPAR sequences of Roldan et al. (1990); panel D shows the chemotactic response to peptide TLVEYYSRASCR (SEQ ID NO:4), a scrambled version of peptide 1.

Figure 5:
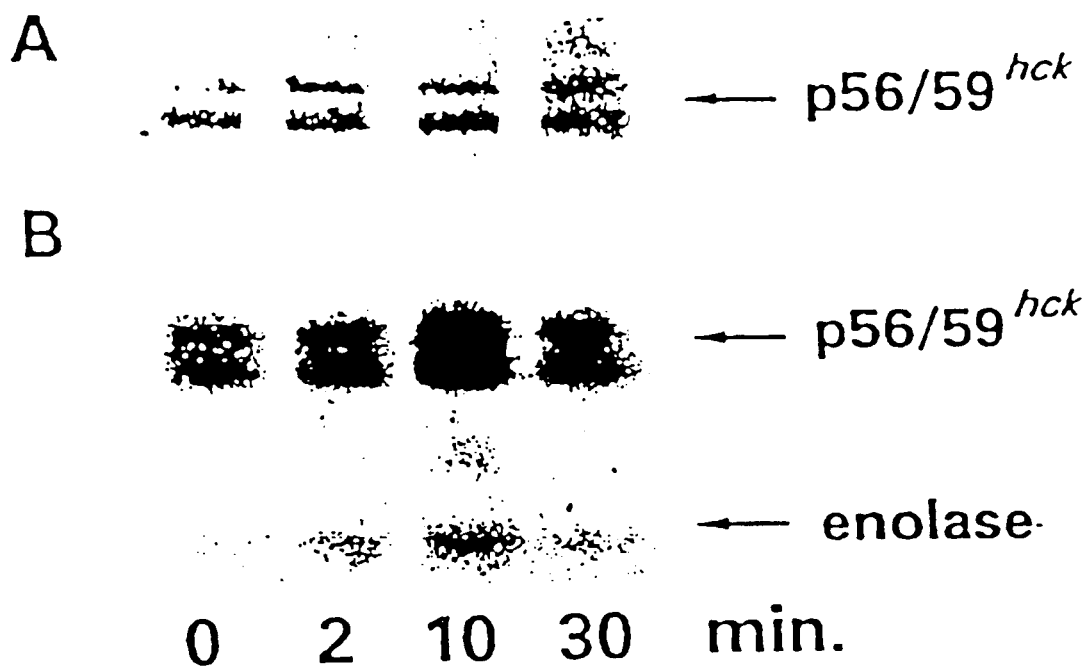

FIG. 5. In this figure, the stimulating effect of peptide 1 on the activity of Hck kinase of THP-1 cells is shown. THP-1 cells were metabolically labelled with [35S]-TransLabel, acid washed, and either mock-treated or treated with 0.1 nM peptide 1 (AVTYSRSRYLEC, (SEQ ID NO:1)) for the indicated time at 37° C. Radiolabelled cell lysates were immunoprecipitated (Resnati et al., 1996) using an affinity-purified rabbit polyclonal anti-p56/p59hck antibody.

(A) An aliquot from each immunoprecipitate was directly analyzed by SDS-PAGE to control that equal amount of p56/p59hck were present during in vitro kinase assay.

(B) The remainder of each immunoprecipitate was subjected to in vitro kinase assay in presence of 5–10 mCi of [g-32P]ATP (~3000 Ci/mmol, Amersham) and 5 mg rabbit muscle enolase for 5 minutes at room temperature. Eluates were thus analyzed by SDS-PAGE autobiography (7.5% acrylamide).

EXAMPLE 1

Chemotactic Response of Human or Murine Cells Stimulated with Fragments of Soluble uPAR or of Soluble Recombinant uPAR Mutants Methods Cloning of Soluble uPAR Mutants In the following description, aminoacid residues are numbered according to the previously published uPAR CDNA sequence (Roldan et al., 1990). Mutant cDNA's encoding soluble uPA receptors were generated by Polymerase chain reaction (PCR). The following oligonucleotides were used for the various constructs:

Construct D1 (1–92): oligonucleotides FRA18 and D1.3'T.

Construct D12 (1–191): oligonucleotides FRA18 and D2.3'T

Construct D123 (1–274): oligonucleotides FRA18 and D3.3'T.

The PCR-products were digested with BclI and ClaI, and cloned in Bluescript SK– (Stratagene) digested with BamHI and ClaI.

To generate the constructs encoding D2 (93–191) and D23 (93–274) the D1 region in the D12 and D123 constructs was deleted by substituting the NruI/NsiI fragment containing the D1 coding region, with a fragment generated by amplifying the uPAR cDNA with the primers FRAl18 and D2.5'T and digested with the same enzymes. To generate the construct encoding D3 (192–275), the D12 region in the D123 construct was deleted by substituting the NruI/NcoI fragment containing the D12 coding region, with a fragment generated by amplifying the uPAR cDNA with the primers FRA18 and D3.5'T and digesting with the same enzymes.

All the mutant receptors were tagged at the carboxyterminus with the peptide sequence HRRASVDYKDDDDK (SEQ ID NO:5) which includes the protein kinase substrate and the FLAGTM epitope by inserting in the carboxy terminal ClaI site a linker made by annealing the two oligonucleotides K/FOcs and K/FOas. This linker was inserted into the ClaI site located at the carboxyterminus of all the constructs. All the recombinant coding regions were amplified with the primers NS1 and 46D, digested with NcoI and transferred to the eukaryotic expression vector pBNSEN digested with NcoI and EcoRV. Oligonucleotides (5'-3'):

FRA18: ATTATACTCGAGGAAGACGTGCAGGGAC-CCCGCGCA; (SEQ ID NO:19)

D1.3'T: TTATCGATGGTAACGGCTTCGGGAATA; (SEQ ID NO:20)

D2.3'T: TTATCGATGGCCATTCTGCGGCAGATT; (SEQ ID NO:21)

D3.3'T: TTATCGATGTGGGTGGTTACAGCCACT; (SEQ ID NO:22)

D2.5'T: AATGCATTCGAGGCCCCAAGAG-GCTGGGA; (SEQ ID NO:23)

D3.5'T: TCCATGGGTGCTGTTCCCCTTGCAGCTG-TAACACTGGCGGCCCCAAGAGGCTGGGA; (SEQ ID NO:24)

K/FOcs: CGACGAGCATCTGTCGACTATAAGGAT-GACGACGACAAGTAA; (SEQ ID NO:25)

K/FOas: CGTTACTTGTCGTCGTCATCCTTAT-AGTCGACAGATGCTCGT; (SEQ ID NO:26)

NS1: CCGCGGAAGAACCCATGGGACTCCCAA; (SEQ ID NO:27)

46D: CAAGCTTACTTGTCGTCGTCATCC. (SEQ ID NO:28)

Expression and purification of recombinant proteins
Semi-confluent COS7 cells were harvested in PBS containing 1 mM EDTA and washed twice with RPMI medium. 0.8 ml cell suspension (1–2×107 cells/ml in RPMI) was transferred to electroporation cuvettes (0.4 cm, Bio-Rad) containing the plasmid DNA (30 µg, 1 mg/ml in water) and electroporated at 960 µF, 240 V in an electroporafor (GenePulser, Bio-Rad). After electroporation, cells were transferred to a T175 flask containing 30 ml of rich medium (DMEM with 100% FCS). The next morning, cells were washed three times with PBS and supplemented with 50 ml of serum free medium (DMEM containing 1 % Nutridoma NS, Boehringer Mannheim). Every 4–5 days, conditioned medium was collected and fresh medium added. Recombinant proteins were purified from the conditioned medium by passage over an anti-FLAGTM affinity column (M2 Affinity gel, Sigma). After washing with PBS, recombinant proteins were eluted with 0.1 M glycine pH 3.0.

Purified D1 (1–87) and D23 (88–274) were prepared by cleavage of D123 with chymotrypsin (Behrendt et al. 1991) followed by passage over the FLAGTM affinity column. D1(1–87) was recovered in the flow-through while the D23(88–274) containing the FLAGTM epitope was retained and later eluted with 0.1 M glycine pH 3.0.

Chemotaxis Assay

Chemotaxis analysis were performed using modified Boyden chambers containing polyvinylpyrrolidone polycarbonate filters (13 mm diameter, 5 mm pore size) coated with collagen type I (100 mg/ml in PBS pH 7.4). The coated filters were washed with medium supplemented with 0.2% bovine serum albumin (BSA) and then placed in the Boyden apparatus. After acid wash, 2×105 THP-1 cells suspended in serum-free medium were added above the filter in the Boyden chamber. Purified mutants were diluted in serum-free medium at the indicated concentrations and added below the filter in the lower chamber. The chambers were incubated in a humidified incubafor at 37° C. in 5% CO2 in air for 90 minutes. Filters were removed, the upper surface scraped free of cells, fixed in methanol and stained with crystal violet. For each set of experiments, migration toward the assay medium served as control (random cell migration) and is referred to as 100% migration. All experiments were performed in triplicate; data are reported as number of cells counted for high power field (ten fields for each condition) and expressed as percentage of the control values. Data points represent the mean of three independent experiments (+SEM). When cells of the fibroblast-type or cancer cells were employed for the assay, the time required for migration was higher and the Boyden chamber were usually incubated overnight.

Results

FIG. 2 shows a schematic representation of the structure of recombinant soluble uPAR and of various mutants generated. Previous studies have shown that a soluble form of uPAR (suPAR) is a potent chemoattractant in different cell lines, also in cells lacking endogenous uPAR (Resnati, et al., 1996). However, activity of suPAR requires chymotrypsin cleavage at Tyr87, between the N-terminal, ligand binding, domain D1 and domain D2+D3. This suggests that a unique conformation, uncovered by chymotrypsin cleavage, is required and must interact with a yet unidentified cell-surface receptor which might act as a transmembrane adaptor. The same mechanism applies to uPA binding to the surface-anchored uPAR.

In order to identify the region of uPAR endowed with chemoattractant activity, we first defined the domain of uPAR responsible for the signalling effect and thus for the interaction with the transmembrane adaptor. We engineered and purified different soluble uPAR mutants and analyzed them for the ability to stimulate chemotaxis on THP-1 cells. It is known that truncation of the carboxy-terminal domain results in the loss of the membrane-anchoring capacity and thus in the secretion of an otherwise active molecule (Masucci et al., 1991); to produce soluble forms of uPAR, the sequence corresponding to aa 275–313 (Roldan et al., 1990) was omitted in all the constructs. FIG. 2 shows the schematic representation of the three-domains entire suPAR (D123) (aa 1–274) and of the four deletion mutants constructed: D23 (aa 93–274), D1 (aa1–92), D2 (aa 93–191) and D3 (aa192–274). A kinase-site, followed by an in-frame FLAGTM epitope was inserted at the C terminus of each mutant. All the constructs were cloned in a modified form of the pBNSEN expression vector, COS7 cells transfected by the calcium phosphate co-precipitation method and secreted uPAR mutants protein purified by affinity chromatography. As a control, the purified D123 protein was digested with chymotrypsin (Resnati et al., 1996) and the corresponding products, D1 (aa 1–87) and D23 (88–274), were separated by an additional round of purification on FLAGTM antibody columns. The details of constructs preparation, the purification method and the system employed to assay chemotaxis are given in the above methods section.

FIG. 3 shows the results of the chemotaxis assays employing derivatives of suPAR D123 as chemoattractants. As predicted by previous results (Resnati et al., 1996), purified uncleaved DI23 was unable to stimulate chemotaxis in THP-1 cells, while chymotrypsin cleavage of this protein conferred a strong chemoattractant property (data not shown). When the products of chymotrypsin cleavage of D123 were purified and analyzed separately, only the D23 fragment (FIG. 3, panel F) (residues 88–274) was able to elicit a dose-dependent chemotactic response, while D1 (1–87) (FIG. 3, panel E) did not influence THP-1 cell migration. However when the domain D1 was produced by recombinant DNA technology (D1–92) was tested, it was unexpectedly found to induce a dose-dependent chemotactic effect (FIG. 3, panel A). The sequence of soluble D1 comprised residues 88–92, while the chymotryptic fragment comprised only the sequence 1–87. Likewise, the recombinant D23 (93–274) failed to induce chemotaxis through the entire concentration range analyzed (FIG. 3, panel B). It was noticed that the sequence 88–92 was missing in this mutant, while it was present in the chymotryptic D23(88–274) fragment. These findings overall indicate that the sequence from amino acid 88 to 92, SRSRY (SEQ ID NO:7), was responsible for the chemotactic effect on THP-1 cell migration. Accordingly, no effect on cell migration was observed when the assay was performed in the presence of comparable doses of purified domain D2(93–191) (FIG. 3, panel C) and D3(192–274) (FIG. 3, panel D), in which the sequence SRSRY was not present. This result was obtained not only with THP-1 cells, but also with other cells like murine 3T3 fibroblasts and murine LB6 cells (data not shown). Therefore the chemotactic effect of uPAR fragments is not species-specific, unlike the binding specificity of uPA to uPAR.

EXAMPLE 2
Chemotactic Response of Human Cells Stimulated with Peptides Derived from Human uPAR To confirm the hypothesis that the sequence SRSRY (SEQ ID NO:7) of human uPAR was responsible for the uPAR-mediated signalling effect and thus for the interaction with one or more adaptors, another set of experiments was performed. Three human uPAR-related peptides were analyzed as inducers of chemotaxis on THP-1 cells: peptide 1 (AVTYSRSRYLEC (SEQ ID NO:1); amino acid sequence 84–95 of human uPAR) and its shorter analogue peptide 2 (SRSRYLEC (SEQ ID NO:3), amino acid sequence 88–95 of human uPAR) were tested as inducers of chemotaxis on THP-1 cells. Numbering of sequence positions follows that of Roldan et al. (1990), in which amino acid residue 1 is the first residue after the signal peptide. The two above peptides both contain the SRSRY (SEQ ID NO:7) motif. The third peptide was chosen in the carboxy terminal region of the uPAR cDNA sequence (YTARLWGGTLLT (SEQ ID NO:2), aa 301–313) and used in the assay as a negative control. An additional peptide was employed to control for the specificity of the effects mediated by the SRSRY (SEQ ID NO:7)-containing peptides. More precisely, a scrambled version of peptide 1 (TLVEYYSPASCR (SEQ ID NO:4)) was also tested under the same experimental conditions. Results of these experiments are shown in FIG. 4. Peptides 1 and 2 were able to elicit a dose-dependent chemotactic effect, with a maximal response at concentrations as low as 0.1 pM (FIG. 4, Panels A and C). On the contrary, when the assay was performed in the presence of similar doses of the control peptide 3, or of peptide TLVEYYSRASCR (SEQ ID NO:4) (peptide 1 in a scrambled sequence), no effect on cell migration was observed over the entire concentration range analyzed (FIG. 4, panels B and D). Thus, peptides containing the motif SRSRY (SEQ ID NO:7) of human uPAR have a potent chemotactic activity and must be responsible for uPAR induced migration.

These peptides represent novel chemotactic agents acting downstream of the uPA/uPAR interaction.

EXAMPLE 3
Peptide 1 (AVTYSRSRYLEC (SEQ ID NO:1)) Affects Chemotaxis Activating p56/p59hck Tyrosine Knase Activity in THP-1 Cells The mixture of chymotrypsin fragments of suPAR, like the uPA/uPAR interaction, induces chemotaxis by transiently activating the p56/p59hck protein kinase (Resnati et al., 1996). If human uPAR-related peptides containing the SRSRY (SEQ ID NO:7) motif induce a chemotactic response on THP-1 cells though the same mechanism exploited by the uPA/uPAR interaction (i.e. by binding to the unidentified adaptor), they should also activate p56/p59hck. THP-1 cells were metabolically labelled with [35S]-TransLabel, acid washed, and either mock-treated or treated with 0.1 nM peptide 1 (AVTYSRSRYLEC (SEQ ID NO:1)) for the indicated time at 37° C. Radiolabelled cell lysates were immunoprecipitated (Resnati et al.,1996) using an affinity-purified rabbit polyclonal anti-p56/p59hck antibody. An aliquot from each immunoprecipitate was directly analyzed by SDS-PAGE to control that equal amount of p56/p59hck were present during in vitro kinase assay (FIG. 5, panel A). The remainder of each immunoprecipitate was subjected to in vitro kinase assay in presence of 5–10 mCi of [g-32P)]ATP (~3000 Ci/mmol, Amersham) and 5 mg rabbit muscle enolase (substrate) for 5 minutes at room temperature. Eluates were thus analyzed by SDS-PAGE autobiography (7.5% acrylamide). As shown in FIG. 5, panel B, an increase in autophosphorylation of p56/p59hck, as well as an increase of phosphorylation of the exogenous substrate, was observed after peptide 1 stimulation. The effect was very rapid, since p56/pS9hck stimulation was already- evident after 2 minutes, reached a maximum after minutes and returned to the basal level 30 minutes after the addition of the peptide. No effect on p56/p59hck activity was observed when 0.1 nM of the corresponding scrambled peptide was used in the assay (data not shown). The time-course of the effect is identical to that observed with the addition of ATF or of chymotryptic uPAR fragments to THP-1 cells and reported previously (Resnati et al., 1996).

EXAMPLE 4
Panning with uPAR-mimicking Peptide and Selection of Inhibitors Thereof Mammalian cells adhere on specially coated plastic plates, but do not adhere when plated onto plastic dishes commonly employed to grow bacteria. However, when those plates are coated with peptide 1 or 2 (or domain D1-1-92) or with recombinant forms of these peptides, they adhere because they express on their surface specific D1(1–92)-binding proteins. The adhesion can be measured.

As a positive control (i.e. to set up the technique), cells (106) exposing a high number of uPAR molecules are used and the panning is carried out on plates coated with a specific anti-uPAR antibody. As a negative control, the same cells but now not expressing uPAR are employed. The cells employed as negative controls are LB6, 32D, 3T3 fibroblasts, B-lymphoid cell lines and others. As positive controls, THP-1 cells, LB6/uPAR, 32D/uPAR and other expressing cell lines are employed.

For the screening assay, the same cells employed as negative controls (106) are used, and the plates are coated with domain D1(1–92) or domain D1(1–87) (control). The ability of the cells to bind to the plates is tested after 30–300 minutes incubation at 37° C. by microscopic inspection, or by staining the plates with Coomassie Blue. The same can be done using different techniques.

The ability of peptides 1- or 2-coated plates to specifically bind the THP-1 cells is the basis for the screening technique, as any compound capable of inhibiting this binding is a potential antiinflammatory agent, inhibiting chemotaxis. For example, peptide 1 or peptide 2 can in fact inhibit adhesion of cells onto D1(1–92), while the scrambled or other peptides cannot. Such compounds, therefore, can be tested as inhibitors of chemotaxis, employing the methods outlined in examples 1–3. Coating can also be carried out with other recombinant forms of the SRSRY (SEQ ID NO:7) sequence in which the epitope is synthesized in fusion with other proteins. Suitable proteins are ferritin (Sidoli et al. (1993)), thioredoxin, GST, beta galactosidase, human serum albumin.

Inhibitors can be selected from phage display libraries of peptides, branched tripeptides combinatorial libraries, libraries of natural or of chemical compounds, and any other potentially exploitable collection of compounds.

REFERENCES

1 Arienti, F., Sule-Suso, J. Belli, F., Mascheroni, L., Rivoltini, L., Melani, C., Maio, M., Cascinelli, N., Colombo, M. P., Parmiani, G. Limited antitumour T-cell response in melanoma patients vaccinated with interleukin-2 gene-transduced allogeneic melanoma cells. Human Gene Ther., 7, 1955–1963 (1996).

2 Behrendt, N., Ploug, M., Patthy, L., Houen, G., Blasi, F. & Danø, K. 1991. The ligand-binding domain of the cell surface receptor for urokinase-type plasminogen activafor. J. Biol. Chem. 266, 7842–7847.

3 Besser, D., Verde, P., Nagamine, Y. and Blasi, F. 1996. Signal transduction and the uPA/uPAR system. Fibrinolysis, 10, 215–237.

4 Bianchi, E., Ferrero, E., Fazioli, F., Mangili, F., Wang, J., Bender, J. R., Blasi, F. and Pardi, R. 1996. Integrin-dependent induction of functional urokinase receptors in primary T lymphocytes. J. Clin. Invest., 98, 1133–1141.

5 Brünner, N., Holst-Hansen, C., Pedersen, A. N., Pyke, C., Høyer-Hansen, G., Foekens, J. and Danø, K. (1996). Urokinase plasminogen activafor receptor in breast cancer. In "Breast Cancer: Adv. in Biol. and Therap.", 6 F. Calvo, M. Crepin and H. Magdelenat, Eds. John Libbey Eurotext, p. 201–207.

7 Cardoso, AA, Desjardin, E, Newman, W, Gerard, C and Sodrowski, J. 1996. CD4-induced interaction of primary HIV-1 gp120 glycoproteins with the chemokine receptor CCR-5. Nature, 384, 179–183.

8 Carmeliet, P. and Collen, D. 1996. Targeted gene manipulation and transfer of the plasminogen and coagulatiion system in mice. Fibrinolysis, 10, 195–214.

9 Cocchi, F., DeVico, A., Garzino-Demo, A., Cara, A., Gallo, R. C. and Lusso, P. 1996. The V3 domain of HIV-1 envelope gp120 glycoprotein is critical for chemokine-mediated blockade of infection. Nature Med., 2, 1244–1247.

10 Danø, K., Blasi, F., Roldan, A. et al. 1990. Urokinase-type plasminogen activator receptor. Intern. Patent Applic., WO 90/12091.

11 Danø, K., Behrendt, N., Brünner, N., Ellis, V., Ploug, M., and Pyke, C. 1994. Fibrinolysis 8, Suppl. 1, 189–203.

12 Fazioli, F. and Blasi, F. 1994. Urokinase-type plasminogen activator and its receptor: a new target for anti-metastatic therapy? T. in Pharmacol. Sci., 15, 25–29.

13 Gudewicz, P. W. and Bilboa, N. 1987. Human urokinase-type plasminogen activafor stimulates chemotaxis of human neutrophils. Biochem. Biophys. Res. Comm., 147, 1176–1181.

14 Gyetko, M. R., Chen, G.-H., McDonald, R. A., Goodman, R., Huffnagle, G. B., Wilkinson, C. C., Fuller, J. A. and Toews, G. B. 1996. Urokinase is required for the pulmonary inflammatory response to Cryptococcus neoformans. J. Clin. Invest., 97, 1818–1826.

15 Gyetko, M. R., Todd III, R. F., Wilkinson, C. C. and Sitrin, R. G. 1994. The urokinase receptor is required for human monocyte chemotaxis in vitro. J. Clin. Invest., 93, 1380–1387.

16 Magnani, P., Paganelli, P., Songini, C., Samuel, A., Sudati, F., Siccardi, A. G., Fazio, F. Pretargeted immunoscintigraphy in patients with medullary thyroid carcinoma. Brit. J. Cancer, 74, 825.831, (1996)

17 Masucci, M.-T., Pedersen, N. and Blasi, F. 1991. A ligand-binding soluble mutant form of the human urokinase plasminogen activator receptor. J. Biol. Chem., 266, 8655–8658.

18 Merrifield R. B., J. Am. Chem. Soc., 85, 2149, (1963)

19 Nykjær, A., Møller, B., Todd III, R. F., Christensen, T., Andreasen, P. A., Gliemann, J. and Petersen, C. M. 1994. Urokinase receptor. An activation antigen in human T lymphocytes. J. Immunol. 152, 505–516.

20 Premack, B. A. and Schall, T. J. 1996. Chemokine receptors: gateways to inflammation and infection. Nature Med., 2, 1174–1178.

21 Resnati, M., Guttinger, M., Valcamonica, S., Sidenius, N., Blasi, F. and Fazioli, F. 1996. Proteolytic cleavage of the urokinase receptor substitutes foir the agonist-induced chemotactic effect. EMBO J., 15, 1572–1582.

22 Roldan, A. L., Cubellis, M. V., Masucci, M. T., Behrendt, N., Lund, L. R., Danø, K., Appella, E., and Blasi, F. 1990. Cloning and expression of the receptor for human urokinase plasminogen activator, a central molecule in cell-surface plasmin-directed p-oteolysis. EMBO J. 9, 467–470.

23 Schall, T. J. and Bacon, K. B. 1996. Chemokines, leukocyte trafficking, and inflammation. Current Op. Immunol., 6, 865–873.

24 Sidoli, A., Tamborini, E. et.al. "Cloning, expression and immunological characterisation of recombinant Lolium perenne allergen Lol p II. "Journal of Biological Chemistry, 268: 21819–21825(1993).

25 Wei, Y. et al. Science 273, 1551–1555 (1996).

What is claimed is:

1. An isolated peptide consisting of the sequence AVTYSRSRYLEC (SEQ ID NO: 1).

2. An isolated peptide consisting of the sequence SRSRYLEC (SEQ ID NO: 3).

3. An isolated peptide consisting of the sequence SRSRY (SEQ ID NO: 7).

4. A recombinant fusion protein, comprising the peptide of claim 1.

5. A recombinant fusion protein, consisting of a peptide consisting of the sequence of SEQ ID NO: 1 and a peptide consisting of the sequence of SEQ ID NO:3.

6. A method of increasing the chemotactic activity of a cell, comprising adding to the environment of said cell a peptide consisting of the sequence SRSRY (SEQ ID NO: 7) at a dosage of 1.0 nM or less, whereby the chemotactic activity of said cell is increased at least 100% with respect to the chemotactic activity of said cell in the absence of said peptide.

* * * * *

SEQUENCE LISTING

<160> NUMBER OF SEQ ID NOS: 28

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence:synthetic
      peptide analogue of the human uPAR

<400> SEQUENCE: 1

Ala Val Thr Tyr Ser Arg Ser Arg Tyr Leu Glu Cys
 1               5                  10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence:synthetic
      peptide analogue of the human uPAR

<400> SEQUENCE: 2

Tyr Thr Ala Arg Leu Trp Gly Gly Thr Leu Leu Thr
 1               5                  10

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence:synthetic
      peptide analogue of the human uPAR

<400> SEQUENCE: 3

Ser Arg Ser Arg Tyr Leu Glu Cys
 1               5

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence:synthetic
      peptide analogue of the human uPAR

<400> SEQUENCE: 4

Thr Leu Val Glu Tyr Tyr Ser Arg Ala Ser Cys Arg
 1               5                  10

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence:synthetic
      peptide analogue of the human uPAR

<400> SEQUENCE: 5

His Arg Arg Ala Ser Val Asp Tyr Lys Asp Asp Asp Asp Lys
 1               5                  10

<210> SEQ ID NO 6
<211> LENGTH: 6
<212> TYPE: PRT
<213> ORGANISM: Artificial Sequence

```
<220> FEATURE:
<223> OTHER INFORMATION: Description of Artificial Sequence:synthetic
      peptide analogue of the human uPAR

<400> SEQUENCE: 6

Phe Leu Ala Gly Thr Met
 1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence:synthetic
      peptide analogue of the human uPAR

<400> SEQUENCE: 7

Ser Arg Ser Arg Tyr
 1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence:synthetic
      peptide analogue of the human uPAR

<400> SEQUENCE: 8

Ser Arg Asn Arg Tyr
 1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence:synthetic
      peptide analogue of the human uPAR

<400> SEQUENCE: 9

Ser Arg Gly Arg Tyr
 1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence:synthetic
      peptide analogue of the human uPAR

<400> SEQUENCE: 10

Ser Gln Ser Arg Tyr
 1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence:synthetic
      peptide analogue of the human uPAR

<400> SEQUENCE: 11

Ser Gln Asn Arg Tyr
 1               5
```

```
<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence:synthetic
      peptide analogue of the human uPAR

<400> SEQUENCE: 12

Ser Gln Gly Arg Tyr
 1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence:synthetic
      peptide analogue of the human uPAR

<400> SEQUENCE: 13

Pro Arg Ser Arg Tyr
 1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence:synthetic
      peptide analogue of the human uPAR

<400> SEQUENCE: 14

Pro Arg Asn Arg Tyr
 1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence:synthetic
      peptide analogue of the human uPAR

<400> SEQUENCE: 15

Pro Arg Gly Arg Tyr
 1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence:synthetic
      peptide analogue of the human uPAR

<400> SEQUENCE: 16

Pro Gln Ser Arg Tyr
 1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence:synthetic
      peptide analogue of the human uPAR
```

-continued

```
<400> SEQUENCE: 17

Pro Gln Asn Arg Tyr
  1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence:synthetic
      peptide analogue of the human uPAR

<400> SEQUENCE: 18

Pro Gln Gly Arg Tyr
  1               5

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 19
attatactcg aggaagacgt gcagggaccc cgcgca                                36

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 20
ttatcgatgg taacggcttc gggaata                                          27

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 21
ttatcgatgg ccattctgcg gcagatt                                          27

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 22
ttatcgatgt gggtggttac agccact                                          27

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence:synthetic
      DNA
```

```
<400> SEQUENCE: 23
aatgcattcg aggccccaag aggctggga                                    29

<210> SEQ ID NO 24
<211> LENGTH: 56
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 24
tccatgggtg ctgttcccct tgcagctgta acactggcgg ccccaagagg ctggga      56

<210> SEQ ID NO 25
<211> LENGTH: 42
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 25
cgacgagcat ctgtcgacta taaggatgac gacgacaagt aa                     42

<210> SEQ ID NO 26
<211> LENGTH: 42
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 26
cgttacttgt cgtcgtcatc cttatagtcg acagatgctc gt                     42

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 27
ccgcggaaga acccatggga ctcccaa                                      27

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 28
caagcttact tgtcgtcgtc atcc                                         24
```